| United States Patent [19] | [11] | 4,258,029 |
|---|---|---|
| Moloney et al. | [45] | Mar. 24, 1981 |

[54] SYNTHETIC ADJUVANTS FOR STIMULATION OF ANTIGENIC RESPONSES

[75] Inventors: Peter J. Moloney; George Wojcik, both of Toronto, Canada

[73] Assignee: Connaught Laboratories Limited, Willowdale, Canada

[21] Appl. No.: 32,570

[22] Filed: Apr. 23, 1979

[51] Int. Cl.³ .................... A61K 39/02; A61K 39/08; A61K 39/12; A61K 39/13

[52] U.S. Cl. ...................................... 424/88; 424/89; 424/92

[58] Field of Search ...................... 560/40; 424/88–92

[56] References Cited

U.S. PATENT DOCUMENTS

| 2,290,174 | 7/1942 | Epstein et al. | 560/40 |
| 2,833,810 | 5/1958 | Kissman et al. | 560/40 |
| 3,412,138 | 11/1968 | Solar et al. | 560/40 |
| 3,538,070 | 11/1970 | Geiger et al. | 560/40 |
| 3,541,201 | 11/1970 | Brown | 424/91 |
| 3,594,471 | 7/1971 | Hertzberger | 424/91 |
| 3,761,585 | 9/1973 | Mullan et al. | 424/91 |
| 3,792,159 | 2/1974 | Green et al. | 424/91 |
| 3,853,954 | 12/1974 | Kaiser et al. | 560/40 |
| 4,070,455 | 1/1978 | Green et al. | 424/91 |

FOREIGN PATENT DOCUMENTS 1466115  1/1967  France ...................... 560/40

*Primary Examiner*—Shep K. Rose
*Attorney, Agent, or Firm*—Sim & McBurney

[57] ABSTRACT

Long chain alcohol esters of amino acids are used as adjuvants in vaccines to provide an improved antigenic capability when compared with conventional adjuvants.

7 Claims, No Drawings

SYNTHETIC ADJUVANTS FOR STIMULATION OF ANTIGENIC RESPONSES

FIELD OF INVENTION

The present invention is concerned with antigen compositions having improved antigenic capability.

BACKGROUND TO THE INVENTION

An "adjuvant" is a substance that itself is often biologically inactive but which, in conjunction with a given antigen, enhances its antigenic capabilities. Adjuvants have been used experimentally in animals for studies on the immune system and in vaccines for improvement of immunological responses, as measured by antibody titres. The enhancing effects have, in many instances, been confirmed by application to humans.

Prior art adjuvants range in type from simple inorganic materials, such as, aluminum phosphate, to complex mixtures, such as, Freund's adjuvant, which is a homogenate of oil, detergent and killed tubercle bacilli.

One advantage of the use of adjuvants in vaccines lies in the fact that the same degree of antibody response can be achieved with a smaller amount of antigen. This advantage is demonstrated in the case of an antigen which must be used at a dosage where marked primary reactivity is shown in order to induce a suitable antibody level. Adjuvants are particularly useful in cases where the antigen alone does not stimulate high levels of antibody. A main function of an adjuvant is to raise the antibody response to levels which will ensure protection against an infectious disease.

Any material used as an adjuvant in vaccines should be non-toxic, relatively easily metabolized and produce little or no skin reaction at the injection site.

SUMMARY OF INVENTION

The present invention provides a novel antigen composition containing certain compounds which have not heretofore been used as adjuvants, which meet the abovenoted requirements for vaccine use and which result in a higher antigenic capability than prior known adjuvants. The present invention utilizes an ester of a long chain alcohol and an amino acid as the adjuvant. Such esters are generally insoluble or only slightly soluble in aqueous solutions at neutral pH.

GENERAL DESCRIPTION OF INVENTION

The long chain alcohol may be any alkanol of the general formula R-OH, where R is an alkyl group containing 12 to 22 carbon atoms. The alkyl group is usually an n-alkyl group, and examples of suitable alcohols include n-decanol, n-dodecanol, myristyl alcohol, cetyl alcohol and n-octadecanol.

The amino acid may be any amino acid of the formula:

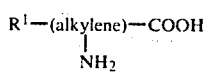

where $R^1$ is hydrogen or an organic group. The alkylene group is usually a (CH) group, i.e., the α-amino acids. Examples of amino acids which may be used include leucine, tyrosine and tryptophane.

A particularly preferred material is the ester of octadecanol and tyrosine, which has been found to be particularly effective.

The esters may be formed by any convenient process. For example, the alcohol and amino acid may be heated together under reflux while hydrogen chloride gas is bubbled through the mixture, followed by pruification and isolation of the ester as the hydrochloride.

An amino acid ester is added to an antigen, which may be bacterial or viral, to provide the compositions of the invention. The use of the octadecyl tyrosine with tetanus toxoid and poliomyelitis vaccine have been found to be particularly effective.

The quantity of adjuvant used depends on the antigen with which it is used and the antigen dosage to be applied. Usually the quantity is within the range conventionally used for adjuvants. For example, in the case of tetanus toxoid, where the normal dose is about 30 Lf/ml, quantities of adjuvant of about 0.3 to about 2 mg/ml may be used.

EXAMPLES

Example 1

This Example illustrates the preparation of octadecyl tyrosine hydrochloride.

Octadecanol (8 g) and l-tyrosine (3 g) were placed in a 250 ml round-bottomed flask together with a magnetic stirring bar. The flask was fitted with a reflux condenser and heated to about 120° C. for 3 hours. During this time the mixture was stirred and dry hydrochloric acid gas continuously bubbled through at a slow rate.

After cooling the mixture, ethyl ether (50 ml) was added. On standing, the mixture formed a slurry which was centrifuged. The precipitate was washed three times with ether to remove octadecanol. The ether-washed precipitate consisted of unreacted tyrosine and octadecyl tyrosine hydrochloride.

The washed precipitate was suspended in water and the pH adjusted to 8.0 to produce the free base. After drying, the precipitate was extracted with ether to dissolve the octadecyl tyrosine free base. Octadecyl tyrosine hydrochloride was obtained by saturating the ether solution with dry hydrogen chloride gas. The yield was 1.25 g of the hydrochloride (yield 16%). Analysis for nitrogen gave 2.96% (calculated 2.98%) giving an estimated purity equivalent to 99%.

Example 2

This Example set forth procedures for the preparation of suspensions of octadecyl tyrosine and antigen.

Procedure A:

Tetanus toxoid solution (10 ml, 30 Lf/ml, pH 7.0) was placed in a container with a magnetic stirring bar. An ether solution of octadecyl tyrosine (0.3 ml, 30 mg/ml) was added, the mixture stirred rapidly and the ether removed under vacuum. The resulting cloudy solution was stirred at room temperature for 24 hours. The supernatant, after centrifuging, contained no detectable tetanus toxoid.

Procedure B:

To tetanus toxoid solution (10 ml, 30 Lf/ml, pH 7.0) was added dry octadecyl tyrosine base (10 mg) and the mixture stirred for 24 hours at room temperature. After this time no detectable tetanus toxoid was found in the supernatant.

Octadecyl tyrosine base dissolved in ether can be sterilized by filtration so that the procedures can be carried out aseptically.

Example 3

Three groups of seven guinea pigs were injected: (1) with tetanus toxoid adsorbed on octadecyl tyrosine, (2) tetanus toxoid adsorbed on aluminum phosphate, and (3) plain tetanus toxoid respectively. After four weeks the animals were bled and the antibody titres determined. All three groups were then given a second dose of unadjuvated tetanus toxoid. Two and one half weeks later they were bled and the antibody titres measured. The results are given in the following Table I:

TABLE I

| Group | 1st Treatment | 2nd Treatment | Antibody Units/ml 4 Weeks | Antibody Units/ml 6½ weeks |
|---|---|---|---|---|
| 1 | 30 Lf Tetanus Toxoid + 1 mg/ml Octadecyl Tyrosine — 1 ml/ subcutaneous | 5 Lf Toxoid 0.5 ml subcutaneous | 2.54 ± 0.4 (7)$^{(a)}$ | 18 ± 2.7 (6) |
| 2 | 30 Lf Tetanus Toxoid + 3 mg/ml AlPO$_4$ — 1 ml/subcutaneous | 5 Lf Toxoid 0.5 ml subcutaneous | 2.35 ± 0.3 (7) | 9.7 ± 1.1 (6) |
| 3 | 30 Lf Tetanus Toxoid 1 ml subcutaneous | 5 Lf Toxoid 0.5 ml subcutaneous | 1.39 ± 0.2 (7) | 7.2 ± 1.2 (6) |

$^{(a)}$The bracketed figures show the number of animals.
Note:
After secondary stimulus (six and one half weeks after first injection) stearyl tyrosine-tetanus toxoid gave a significantly greater antibody response than did tetanus toxoid without adjuvant ($p < .01 > .0001$); and a better response than AlPO$_4$ tetanus toxoid ($p < .05 > .01$).

It can be seen that after four weeks there is very little difference in the titres of the three groups. However, after the second injection there is a very significant difference in the antibody titres in the group receiving their primary stimulus with toxoid containing the octadecyl tyrosine. The footnote to Table I indicates the degrees of significance.

Example 4

Six guinea pigs which had been sensitized to tetanus toxoid were tested for local skin reactions. Three tetanus toxoids were used for the test: unaltered toxoid, heptadecylamine toxoid and octadecyl tyrosine toxoid. Animals were given 2 Lf in 0.1 ml and the diameters of the reactions read 20 hours after the injections. The results are shown in the following Table II:

TABLE II

| | Material | Dose | Diameter in mm |
|---|---|---|---|
| 1. | Unaltered Tetanus Toxoid | 2 Lf/0.1 ml | 17 ± 1.47 (6) |
| 2. | Heptadecylamine Tetanus Toxoid | 2 Lf/0.1 ml | 11 ± 0.97 (6) |
| 3. | Octadecyl Tyrosine Toxoid | 2 Lf/0.1 ml | 8.3 ± 0.67 (6) |

The diameters obtained for the octadecyl tyrosine toxoid reported in the above Table II were statistically smaller than those obtained for the other toxoids.

Example 5

The animals remaining from Example 3 were examined for evidence of reaction at the site of the subcutaneous injections. With the guinea pigs that had received toxoid plus aluminum phosphate there were distinctly palpable nodules of diameter about 8 mm. With the guinea pigs receiving octadecyl tyrosine very small nodules of diameter 2 to 3 mm only were detected in some, but not all, guinea pigs. It should be noted that while the aluminum phosphate was added at a concentration of 3 mg/ml and the octadecyl tyrosine contained only 1 mg/ml, the octadecyl tyrosine toxoid was a better adjuvant at this level than the aluminum phosphate.

Example 6

Three different preparations namely, plain unadsorbed poliomeylitis vaccines (Types 1, 2 and 3), the same poliomyelitis vaccine containing aluminum phosphate as adjuvant and poliomyelitis vaccine containing octadecyl tyrosine. Each preparation was injected into groups of 8 guinea pigs each as undiluted vaccine and at 1/10 and 1/100 dilutions. Four weeks after injection the animals were bled, antibody levels were measured and a secondary stimulus of plain poliomyelitis vaccine injected. After a further three weeks the animals were bled and antibody levels determined. The results are shown in the following Table III:

TABLE III

| Preparation | Potency Relative to Unadsorbed Vaccine$^{(1)}$ Type 1 | Type 2 | Type 3 |
|---|---|---|---|
| Poliomyelitis Vaccine with Octadecyl Tyrosine | 13.8 | 3.24 | 8.51 |
| Poliomyelitis Vaccine with Aluminum Phosphate | 2.63 | 1.66 | 6.17 |

Note:
$^{(1)}$Determined by comparison of ED$_{50}$

It is evident from the results of the above Table III that the vaccine containing octadecyl tyrosine gave higher antibody response than either of the other two preparations. If the results are assessed in terms of relative potency of the vaccines, the octadecyl tyrosine is 13.8, 3.2 and 8.5 times more potent than the plain vaccine for types 1, 2 and 3 respectively. It is more potent than the vaccine containing aluminum phosphate by factors of 5.2, 1.9 and 1.4 for the three virus types.

These results imply that a considerable saving of vaccine could be realized using the octadecyl tyrosine adjuvanted material without loss of efficacy.

SUMMARY OF DISCLOSURE

In summary of this disclosure, the present invention provides a new adjuvant for antigenic compositions which is more effective than conventional adjuvants. Modifications are possible within the scope of this invention.

What we claim is:

1. In a composition comprising at least one bacterial or viral antigenic species and at least one adjuvant in an amount effective to enhance the antigenic response of said antigenic species, the improvement wherein said adjuvant is an ester of a long chain alcohol containing 12 to 22 carbon atoms in the alkyl group and an amino acid.

2. The composition of claim 1 wherein said amino acid is an α-amino acid.

3. In a composition comprising at least one bacterial or viral antigenic species and an adjuvant in an amount effective to enhance the antigenic response of said antigenic species, the improvement wherein said adjuvant is octadecyl tyrosine.

4. The composition of claim 1, 2 or 3 wherein said antigenic species is tetanus toxoid.

5. The composition of claim 1, 2 or 3 wherein said antigenic species is poliomyelitis vaccine.

6. The method of administration of antigenic species to a warm blooded animal, which comprises:
 (a) injecting the animal with a dose of a composition comprising at least one bacterial or viral antigenic species and at least one ester of a long chain alcohol containing 12 to 22 carbon atoms in the alkyl group and an amino acid as adjuvant in an amount at least effective to provide an enhanced antigenic activity in said animal following completion of said administration; and subsequently
 (b) injecting the animal with a dose of said at least one bacterial or viral antigenic species.

7. The method of claim 6 wherein said antigenic species is poliomyelitis vaccine and said ester is octadecyl tyrosine.

* * * * *